United States Patent [19]

Bay et al.

[11] Patent Number: 4,618,720

[45] Date of Patent: Oct. 21, 1986

[54] PREPARATION OF ALKYLDIARYLPHOSPHINES

[75] Inventors: W. Elliott Bay, Ridgefield, Conn.; Karl E. Reineke, Mohegan Lake; Edward D. Weil, Hastings-on-Hudson, both of N.Y.

[73] Assignee: Stauffer Chemical Company, Westport, Conn.

[21] Appl. No.: 707,713

[22] Filed: Mar. 4, 1985

[51] Int. Cl.$^4$ .............................................. C07F 9/50
[52] U.S. Cl. ...................................................... 568/17
[58] Field of Search ........................................ 568/17

[56] References Cited

U.S. PATENT DOCUMENTS 3,322,542 5/1967 Ullmann et al. .
3,499,039 3/1970 Lorenz et al. .
3,751,481 8/1973 Weinberg ............................. 568/17
4,166,824 9/1979 Henderson .

OTHER PUBLICATIONS

Grim et al., J. Org. Chem. 32, 781–784 (1967).
"The Preparation and Reactions of Diphenylphosphinous Chloride" by C. Stuebe et al., J. of the Amer. Chem. Soc., vol. 77, pp. 3526–3529 (1955).
"The Free Radical Addition of Phosphines to Unsaturated Compounds" by M. M. Rauhut, The Journal of Organic Chemistry, vol. 26, pp. 5138–5143 (1961).
"Diphenyl(trimethylsilyl)phosphine and Dimethyl(trimethylsilyl)phosphine" by R. Goldsberry and K. Cohn, in Organic Syntheses vol. XIII, pp. 26–29 (1972).
"Diverse Donor Properties Exhibited by the Facultative Diphosphine Diether Ligand, 1,8-Bis(diphenylphosphino)-3,3-Dioxaoctane: Six- and Four-Coordinate Complexes and Trans Bidentate Behaviour" by William E. Hill et al., J. Chem. Soc. Dalton Trans (1982) pp. 833–839.

Primary Examiner—Helen M. S. Sneed

[57] ABSTRACT

An improved process is disclosed for preparing alkyldiarylphosphines and related compounds. Typically, diphenylphosphinous chloride is reacted in solution with an excess of an alkali metal; and the reaction product reacted with chlorohexane thereby forming hexyldiphenylphosphine. The improved process obtains greater yields, by use of critical amounts of alkali metal; use of a single reactor rather than two reactors; preinitiation of the first stage reaction; reduction of temperatures to increase reaction rate under certain conditions; and preferred reactants and physical form thereof. Novel products include behenyldiphenylphosphine.

52 Claims, No Drawings

PREPARATION OF ALKYLDIARYLPHOSPHINES

BACKGROUND (i) Field of the Invention

This invention relates generally to an improved process for preparing alkyldiarylphosphines and related compounds. The related compounds include those wherein the phosphorus atom is replaced by any other trivalent atom from Group VA of the Periodic Table. More particularly, the invention relates to a first step of a process in which a first halide (such as diphenylphosphinous chloride) is reacted in solution with an excess of an alkali metal (such as molten sodium). The second step of the process concerns reacting the reaction product of the first stage with a second halide (such as chlorohexane) thereby forming hexyldiphenylphosphine which is thereafter separated. The improvement features particularly relate to greater yield, use of critical amounts of alkali metal, and a single reactor rather than two reactors. Novel products prepared by the process include behenyldiphenylphosphine.

(ii) Description of the Prior Art

A computer search of Chemical Abstracts over the period 1967 to present, turned up only three references directed to n-hexyldiphenylphosphine and having the corresponding CA code number "RN-18298-00-5". None of these references relate to processes for preparing phosphines (or related products such as arsines), but rather to their properties and utility, as summarized below.

U.S. Pat. No. 3,322,542 (Ullmann et al) is entitled "Stabilization Additives for Photochromic Compounds". Its Example 49 relates to the use of "diphenylhexylphosphine" (DPHP) as such an additive, and a number of the other examples relate to the use of other phosphines.

"Allylic Alkylations Catalyzed by Nickel" by Cuvigny et al. in *J. Organomet. Chem.*, 250(1), C21–C24, apparently also refers to the use of hexyldiphenylphosphine as a catalyst for allylic alkylation of enolates.

"Carbon-13 NMR Spectra of Tertiary Phosphines, Arsines, and their Onium Salts" by Koketsu in "Physical Organic Chemistry", Vol. 12, at pages 1836–43 reports the 13C-NMR spectra for compounds containing a phosphorus or arsenic atom, including alkyldiphenylphosphines such as hexyldiphenylphosphine.

"The Preparation and Reactions of Diphenylphosphinous Chloride" by C. Stuebe et al. in *J. of the Amer. Chem. Soc.*, Vol. 77, pgs. 3526–3529 (1955) includes a method of preparing hexyldiphenylphosphine at pgs. 3527–3528. It points out that diphenylphosphinous chloride reacts readily with Grignard reagents to give tertiary phosphines in good yield. From FIG. 1, a "good yield" appears to be 70–75%. It is believed that this reaction would not be easy to run on a plant scale.

"The Free Radical Addition of Phosphines to Unsaturated Compounds" by M. M. Rauhut in *The Journal of Organic Chemistry*, Vol. 26, pages 5138–5143 (1961) describes the preparation of octyldiphenylphosphine by the free radical initiated addition of diphenylphosphine to 1-octene, and other related compounds. This reaction is generally low yielding and difficult to carry to completion.

In addition to the foregoing, three references are known which disclose 2-step processes having some similarities to the invention claimed hereinafter. They are discussed below.

"Diphenyl(trimethylsilyl)phosphine and Dimethyl(trimethylsilyl)phosphine" by R. Goldsberg and K. Cohn in *Organic Syntheses* Volume XIII, published by McGraw-Hill, (1972), at pages 26–29 states that diphenyl(trimethylsilyl)phosphine has been prepared in yields above 60% by the reaction of chlorotrimethylsilane with sodium diphenylphosphide in constantly refluxing n-butyl ether. The sodium diphenylphosphide is prepared from commercially available diphenylphosphinous chloride. Although the initially formed product is the tetraphenyldiphosphine, the phosphorus-phosphorus bond is cleaved by the action of excess sodium to give the sodium salt. The stated reactions are shown below.

(Reaction 1A)
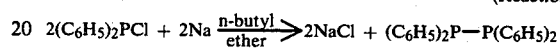

(Reaction 1B)
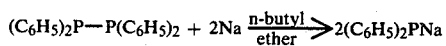

(Reaction 2)
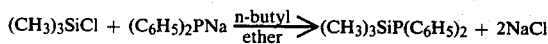

The working Example described at pages 27 and 28 used about 120% excess sodium in the first step of the process (since 0.65 mole of sodium was used in conjunction with 0.15 mole of diphenylphosphinous chloride, rather than the 0.30 mole of sodium theoretically needed for the reaction). Further, the suspension of sodium diphenylphosphide was transferred to a separate vessel prior to the commencement of the final reaction and the excess sodium remained behind in the original vessel.

"Diverse Donor Properties exhibited by the Facultative Diphosphine Diether Ligand, 1,8-Bis(diphenylphosphino)-3,6-dioxaoctane: Six- and Four-coordinate Complexes and trans Bidentate Behaviour" by William E. Hill et al. in *J. Chem. Soc. Dalton Trans.* (1982) at pages 833–839 also discloses a first-step process including the preparation of sodium diphenylphosphide slurry. The working example (at the bottom of page 837 and the top of page 838) indicates that 0.65 mole of sodium metal was used in conjunction with 0.10 mole of diphenylphosphinous chloride. Further, the diphenylphosphide slurry was transferred to a separate vessel and implicitly the excess sodium remained in the original vessel prior to the next step of the process.

U.S. Pat. No. 4,166,824 (Henderson) relates to a chiral biphosphine-rhodium complex as a catalyst for the asymmetric reduction of a tetramisole precursor which allows the synthesis of levamisole in high optical yield. Example 5 is hereby incorporated by reference. It includes a description of the preparation of an intermediate product mixture containing sodium diphenylphosphide and unreacted sodium. The "ditosylate product of Example 4" was added to the foregoing intermediate product in situ. However, it appears that (1) the percent yield of the final product (i.e., "Formula 1 in Sequence 1") was extremely low; (2) the unreacted sodium corresponded to at least 100 percent excess; (3) the "ditosylate product of Example 4" is not a halide; and (4) the particle size of the sodium is not indicated.

Essentially, nowhere does the prior art disclose or suggest the type of process claimed hereinafter wherein the amount of excess sodium is less than 100% or wherein the conversion efficiency is greater than 70%.

SUMMARY OF THE INVENTION

In contrast to the aforementioned prior art it has now been surprisingly discovered that the overall yield of a 2-step process for preparing hexyldiphenylphosphine and related products can be increased to over 90% by using the process claimed hereinafter. In its broadest aspect, the invention is:

An improved two-step process for preparing a compound C3 having the structural formula

wherein:
Z is an atom from Group VA of Merck's Periodic Table;
Y is any radical that is essentially incapable of reacting with an alkali metal;
X is any radical that is essentially incapable of reacting with an alkali metal;
W is a substituted or unsubstituted aryl, alkyl, arylalkyl, or alkylaryl radical or hydrogen; and
U is hydrogen or

or halogen; by a first step comprising converting a first compound, C1, into a second compound, C2; and a second step comprising converting C2 into a third compound, C3; wherein the first step comprises reacting a first halide C1, with a molten alkali metal, M, or amalgam thereof, in the presence of an inert solvent, S, to form a first reacted mixture comprising C2; and the second step comprises reacting C2 with a second halide, W-"H2" or "H2"-W-"H2", to form a second reacted mixture comprising C3; all wherein (i) C1 has a structural formula

wherein:
X,Y,Z are as defined above: and
"H1" is a halogen atom; and
(ii) C2 has a structural formula

wherein: X,Y,Z and M are as defined above:
(iii) "H2" is a halogen atom; and
(iv) W is as defined above; wherein the improvement comprises using an amount of M such that the first reacted mixture comprises an excess of M in an amount of less than 100%, and wherein the yield of C3 is greater than 70 percent.

DESCRIPTION OF THE PREFERRED EMBODIMENTS

The process of the present invention is illustrated by, but not limited to, the working examples below directed to the preparation of n-hexyldiphenylphosphine; n-eicosyl diphenylphosphine; behenyldiphenylphosphine; and related products.

In practicing the invention, it is most preferred that "Z" be phosphorus. However, Z may be any atom from Group VA of Merck's Periodic Table, found in *The Merck Index*, 10th Edition, 1983. When Z is nitrogen, additional safety precautions would have to be taken. It is well known that many nitrogen-halides are explosive, and standard techniques for handling these materials would be needed.

In all the Examples, Y and X are phenyl. However, it is sufficient that X and Y merely be essentially incapable of reacting with an alkali metal. For example, they should not be substituted with halogen, hydroxyl, or acidic groups.

W is most preferably alkyl as in all the Examples. When W is aryl or substituted-aryl, it is likely that lower rates of reaction will be present in the second stage of the process. Essentially, the limitations on the substituents in W are the same as for the substituents in X and Y.

It is preferred that "H1" and "H2" be chlorine or bromine, most preferably chlorine.

Typical preferred "C3" compounds that may be prepared by this invention include the following; compounds having both high melting point and high boiling point, particularly alkyldiphenylphosphines and -arsines wherein the alkyl group contains from 1 to 40 carbons. The compounds may contain substituents except those that react with alkali metals; therefore the substituents can not be halogen, hydroxyl or acidic groups. However, the compound may be an ether, a silyl, or a tertiary amine.

The foregoing "C3" compounds are preferably prepared from "C1" and "C2" compounds wherein the halogen atom is chlorine or bromine.

A large number of different inert solvents, S, may be used in this invention. It is merely sufficient that the solvent have the following characteristics. Its boiling point is preferably higher than the melting point of the metal M or amalgam. It is preferably water-immiscible, because of subsequent separation procedures. It may be polar (such as di-n-butyl ether) or nonpolar (such as toluene). Ethanol is unsuitable because it reacts with alkali metals. Such solvents typically include di-n-butyl ether, toluene, tetrahydrofuran, and p-dioxane.

In the practice of this invention, it is essential that the amount of excess metal, M, or amalgam present in the first reacted mixture be in an amount of less than 100%. This is true even though the cost of the metal is normally insignificant compared with the cost of the reactants used in the process. More preferably the excess of M is less than 50% by weight, and most preferably less than 40%. At least when the scale of reaction is relatively small (say 10 moles) it is preferred that the excess of M be more than 5% by weight, in order to reduce the amount of oxide present.

It is preferred that M be in the form of particles having diameters less than 5,000 microns, most preferably less than 1,000 microns. Such fine particles may, if desired, be prepared by passing them through a conventional homogenizer.

A number of other preferred embodiments are disclosed in the examples which follow. These embodiments include (1) initiating the first reaction by adding up to about 5% of a molar amount of the first halide; and (2) temporarily reducing the temperature of the first reaction to a temperature that is a few degrees above the melting point of M or amalgam (thereby helping to break up the precipitate which has coated M with reaction products and, in turn, generating new surface area for the metal M).

Novel products made by this invention include behenyldiphenylphosphine, a waxy solid. This product is particularly pure with regard to normal alkyl phosphines, and therefore particularly suitable for ligands.

Finally it should be noted that when C1 is a solid, it is normally desirable to dissolve it in a solvent (particularly the same solvent as used in the reaction) to permit its gradual addition in a controllable manner.

COMPARATIVE EXAMPLE C-1

This Comparative Example is not prior art. It illustrates the relatively low yield obtained (18 percent) when a large amount of excess sodium is used and when the excess sodium is removed prior to commencement of the conversion of the phosphide to the phosphine by transferring the phosphide slurry to a second vessel.

Distilled di-n-butyl ether (1100 ml) and solid sodium metal (124.1 g, 5.4 moles) were placed in a 5 L round bottom flask. The flask was fitted with a reflux condenser, efficient overhead stirrer, addition funnel, thermometer, and a heating mantle. The entire reaction was conducted under an atmosphere of dry nitrogen.

The butyl ether was heated to reflux (about 140° C.) and the now-molten sodium stirred vigorously to produce an emulsion of sodium in the solvent. Diphenylphosphinous chloride (485 g, 2.2 moles) was added dropwise at a very slow rate to initiate the reaction. [It should be noted that if addition is too fast, the molten sodium will become coated with a dark grey material. Once this coating occurs it is very difficult to get the reaction to start. The reaction is initiated when the bright yellow-green color of the sodium diphenylphosphide salt appears in the solution. If this has not occurred after the first 2% of the diphenylphosphinous chloride has been added then the addition should be stopped until the green color of the salt appears. Waiting for 15–30 minutes is usually all that is necessary to initiate the reaction.] The remainder of the diphenylphosphinous chloride was then added at such a rate that the reflux was controllable. This addition took about 1.5 hours and the voltage on the heating mantle had to be reduced in order to control the reaction.

The voltage on the heating mantle was increased after addition was complete in order to maintain the reaction at reflux. Stirring at reflux was continued for 2 hours. At this point the reflux and stirring were both stopped and the solids along with the remainder of the molten sodium allowed to settle to the bottom of the flask. The clear liquid above the solids was transferred (while it was still warm) with a cannula into a clean, dry, nitrogen-filled 5 L flask. This flask was fitted with a reflux condenser, overhead stirrer, addition funnel, and a thermometer. The solids and excess sodium in the first flask were destroyed with ethanol and water and discarded. The transferred solution was cooled to room temperature and n-hexyl chloride (278 g, 2.31 moles) was added with stirring at such a rate that the reaction temperature did not exceed 70° C. Stirring was continued for 30 minutes after addition was complete. Water (1200 ml) was then added in one portion and the slurry stirred until the inorganic salts dissolved. The mixture was poured into a 2 L separating funnel and the lower aqueous layer drained and discarded. The organic layer was dried over magnesium sulfate and concentrated giving crude n-hexyldiphenylphosphine (109 g, 0.40 mole) in an 18% yield based on diphenylphosphinous chloride.

EXAMPLE 1

This Example illustrates the high yields that may be obtained by using 0% excess sodium and completing the second and final state of the process in situ. However, the product had a high phosphine oxide content.

Distilled di-n-butyl ether (2500 ml) and solid sodium metal (230 g, 10.0 moles) were placed in a 22 L round bottom flask. The flask was equipped as in the above Comparative Example C-1. The solution of the sodium phosphide salt was made by carefully adding diphenylphosphinous chloride (1100 g, 5.0 moles) to the refluxing solvent-sodium slurry as described in the previous example. Stirring and reflux was continued for 2 hours after addition of the diphenylphosphinous chloride was complete. The reaction mixture was cooled with further stirring to about 45° C. n-Hexyl chloride (603 g, 5 moles) was added over a 30 minute period. Stirring was continued for 30 minutes after this addition was complete. Water (2500 ml) was added with stirring and the inorganic salts dissolved. Stirring was stopped and the lower water layer drained off and discarded. The upper organic layer was concentrated under vacuum giving crude n-hexyldiphenylphosphine (1190 g) of about 87 percent yield based on diphenylphosphinous chloride. This material was found to be about 20 percent n-hexyldiphenylphosphine oxide by GLC analysis.

EXAMPLE 2

This Example illustrates the high yields and low phosphine oxide content obtained when the amount of excess sodium is about 34% and the final stage reaction is completed in situ without removal of the excess sodium until after completion of the final reaction.

Distilled n-butyl ether (2500 ml) and solid sodium metal (310 g, 13.5 moles) were placed in a 22 L round bottom flask. The flask was equipped as in Comparative Example C-1. The solution of the sodium diphenylphosphide salt was made by carefully adding diphenylphosphinous chloride (1100 g, 5.0 moles) to the refluxing solvent and molten sodium slurry as previously described. Stirring at reflux was continued for 2 hours after addition of the diphenylphosphinous chloride was complete. During this time a brown pasty precipitate formed. Most of the particulate material in the reaction mixture was entrained in this mass. This precipitate also entrained any remaining sodium and slowed the rate of reaction. To overcome this difficulty the reaction temperature was lowered to about 100°–110° C. which is slightly above the melting point of sodium, (i.e., 97.6° C.). At this temperature the precipitate solidified and broke up into a finely divided slurry. The remainder of the sodium was then mobile enough to complete the reaction. Stirring at this lower temperature was continued for another 2 hours. (It is believed to be surprising that reaction rate is increased by reducing temperature.)

The heating mantle was then removed and the solution allowed to cool to 45°–50° C. with stirring. n-Hexyl chloride (634 g, 5.26 moles) was added at a rate such that the reaction temperature did not exceed 70° C. This addition required about 30 minutes, and stirring was continued for a further 30 minutes after addition was complete.

The reaction mixture was cooled to 40°–45° C. and methanol (200 ml, about 5 moles) was added very cautiously. The addition rate was such that the vessel temperature did not exceed 50° C. and the evolution of hydrogen was controllable. After hydrogen evolution ceased (about 15 minutes after the addition of methanol was complete) about 20–30 ml of water was added. The reaction was stirred for 5 minutes and very little gassing of the reaction was observed. Additional water was added in one portion to bring the total volume of water added to 1875 ml. Stirring was continued until all the salts dissolved (after about 20 minutes). Stirring was stopped and the solution allowed to separate into layers. The bottom water layer was removed and discarded. The solvent was stripped from the remaining product by rotary evaporation. The last traces of solvent were removed by vacuum distillation at 150° C. vessel temperature and 20–25 mm Hg absolute pressure. The vessel residue was cooled and filtered through CELITE in a sintered glass funnel to remove the small amounts of solids present. The final weight of n-hexyldiphenylphosphine was 1170 g (greater than 90% yield based on diphenylphosphinous chloride). This material was <1% phosphine oxide.

EXAMPLE 3

This Example is largely similar to Example 2, except that the second halide is one which contains 20 carbon atoms rather than 6 carbon atoms.

Distilled di-n-butyl ether (30 ml) and sodium (3.44 g, 149.6 mmoles) were placed in a 250 ml round bottom flask under a nitrogen atmosphere. The flask was equipped with a reflux condenser, efficient overhead stirrer, addition funnel, thermometer, and heating mantle. The solution of the sodium diphenylphosphide salt was made by carefully adding diphenylphosphinous chloride (12.2 g, 55.3 mmoles) to the refluxing solvent-molten sodium slurry as described in the previous examples. Stirring and reflux were continued for 2 hours after addition of the diphenylphosphinous chloride was complete. The reaction mixture was cooled with stirring to 45° C. n-Eicosyl bromide (a wax) was dissolved in di-n-butyl ether (20 g, 55.4 mmoles, 14 ml) and the solution was added dropwise to the foregoing reaction mixture. The temperature rose from 45° to 57° C. After the exotherm subsided, methanol (5 ml) was added slowly. Water (45 ml) was added after gassing of the reaction mixture stopped. Stirring was stopped and layers were allowed to form. The lower aqueous layer was separated and discarded. The solvent was removed from the upper organic layer by distillation. The crude n-eicosyldiphenylphosphine solidified on cooling, giving 24.03 g of a white waxy solid. The yield was 93% based on diphenylphosphinous chloride.

EXAMPLE 4

This Example is largely similar to Example 3. However, it illustrates the fact that C2 may be a mixture of halides containing different numbers of carbon atoms.

Example 3 was repeated except that behenyl bromide was used in place of n-eicosyl bromide. The approximate composition of the behenyl bromide was: about 75% with 22 carbon atoms in the aliphatic side chain; about 17% with 20 carbon atoms; and about 8% with 18 carbon atoms.

The final product had the composition given below. The analysis of the phosphonium halide is based on inorganic halide titration. The other values are based on GC area %.

| | |
|---|---|
| Alkyldiphenylphosphine | 93% |
| Alkyldiphenylphosphine Oxide | 0.8% |
| Diphenylphosphine | 0.5% |
| Dialkyldiphenylphosphonium Halide | 3% |

It should be noted that the presence of dialkyldiphenylphosphonium halide as byproduct came as a surprise, since it had not been found in Examples 1 and 2. It is believed that the amount of this byproduct could be reduced by use of lower temperatures and/or dilution with more solvent.

COMPARATIVE EXAMPLE 5C TO EXAMPLE 24 n-Hexyldiphenylphosphine was prepared in a series of twenty experiments, as partly summarized in Tables 1A and 1B below. Yields ranged from 50 to 96%. The following experimental conditions differed in part from those of Example 2.

The amount of excess sodium ranged from 0 to 100% (see Table 1A).

The second halide was n-hexyl chloride except for Example 9 when the bromide was used (Table 1B).

The second halide was added to the first reacted mixture in situ, except in Examples 7C and 18C when the first reacted mixture was transferred in part to a second vessel after removal of the excess sodium, prior to the addition of the second halide (Table 1B).

The solvent used was di-n-butyl ether, except for Examples 6C and 10 which used toluene (Table 1B).

The scale of experimentation ranged from 0.08 mole to 10 moles.

TABLE 1A

| YIELDS OF n-HEXYLDIPHENYLPHOSPHINE | | | | |
|---|---|---|---|---|
| Example | Crude Yield | % Oxide | Na/DPC | % Excess Na |
| 5C | 58% | — | 2:1 | 0% |
| 6C | 50% | — | 4:1 | 100% |
| 7C | 65% | 4% | 4:1 | 100% |
| 8 | 84% | 12% | 2.5:1 | 25% |
| 9 | 89% | — | 2.5:1 | 25% |
| 10 | 99% | 9% | 2.5:1 | 25% |
| 11 | — | 25% | 2.5:1 | 25% |
| 12 | — | 30% | 2.5:1 | 25% |
| 13 | — | 23% | 2:1 | 0% |
| 14 | 88% | 20% | 2:1 | 0% |
| 15 | — | 7.5% | 2.1:1 | 5% |
| 16 | — | 24% | 2.1:1 | 5% |
| 17 | — | 3% | 2.7:1 | 35% |
| 18C | 18% | 10% | 2.45:1 | 23% |
| 19 | 87% | 9% | 2.2:1 | 10% |
| 20 | 92% | 0.7% | 2.7:1 | 35% |
| 21 | 93% | 1.1% | 2.6:1 | 30% |
| 22 | — | 2% | 2.6:1 | 30% |
| 23 | 94% | <1% | 2.7:1 | 35% |
| 24 | 96% | <1% | 2.7:1 | 35% |

TABLE 1B

| YIELDS OF n-HEXYLDIPHENYLPHOSPHINE | | | | |
|---|---|---|---|---|
| Example | # Vessels | Scale (Mole) | Halogen in Hexyl Halide | Solvent |
| 5C | 1 | 0.08 | Cl | Bu₂O |

TABLE 1B-continued
YIELDS OF n-HEXYLDIPHENYLPHOSPHINE

| Example | # Vessels | Scale (Mole) | Halogen in Hexyl Halide | Solvent |
|---|---|---|---|---|
| 6C | 1 | 0.08 | Cl | $PhCH_3$ |
| 7C | 2 | 0.4 | Cl | $Bu_2O$ |
| 8 | 1 | 0.4 | Cl | $Bu_2O$ |
| 9 | 1 | 0.2 | Br | $Bu_2O$ |
| 10 | 1 | 0.2 | Cl | $PhCH_3$ |
| 11 | 1 | 0.1 | Cl | $Bu_2O$ |
| 12 | 1 | 0.1 | Cl | $Bu_2O$ |
| 13 | 1 | 0.2 | Cl | $Bu_2O$ |
| 14 | 1 | 5 | Cl | $Bu_2O$ |
| 15 | 1 | 0.4 | Cl | $Bu_2O$ |
| 16 | 1 | 0.4 | Cl | $Bu_2O$ |
| 17 | 1 | 0.4 | Cl | $Bu_2O$ |
| 18C | 2 | 2.2 | Cl | $Bu_2O$ |
| 19 | 1 | 0.4 | Cl | $Bu_2O$ |
| 20 | 1 | 0.4 | Cl | $Bu_2O$ |
| 21 | 1 | 0.4 | Cl | $Bu_2O$ |
| 22 | 1 | 0.4 | Cl | $Bu_2O$ |
| 23 | 1 | 5 | Cl | $Bu_2O$ |
| 24 | 1 | 10 | Cl | $Bu_2O$ |

PROPOSED EXAMPLE 25

In a like manner to Examples 3 and 4, one-half molar equivalent of 1,12-dibromododecane is reacted with one molar equivalent of the sodium salt of diphenylphosphine to produce $(C_6H_5)_2P(CH_2)_{12}P(C_6H_5)_2$, a waxy colorless solid.

Finally, it will be appreciated that, although all the foregoing Examples relate to C1 compounds which are monohalophosphines, many aspects of the invention are likely to be applicable to the use of C1 compounds which are dihalo- or trihalophosphines.

What we claim is:

1. An improved two-step process for preparing a compound C3 having the structural formula

wherein:
Z is phosphorus;
Y is aryl;
X is aryl;
W is a substituted or unsubstituted aryl, alkyl, arylalkyl, or alkylaryl radical or hydrogen; and
U is hydrogen or

or halogen; by a first step comprising converting a first diphenylphosphinous halide compound, C1, into a second compound, C2; and a second step comprising converting C2 into a third compound, C3; wherein the first step comprises reacting a first halide C1, with a molten alkali metal, M, or amalgam thereof, in the presence of an insert solvent, S, to form a first reacted mixture comprising C2; and the second step comprises reacting C2 with a second halide, W-"H2" or "H2"-W-"H2", to form a second reacted mixture comprising C3; all wherein
(i) C1 has a structural formula

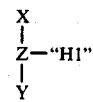

wherein:
X,Y,Z are as defined above: and
"H1" is a halogen atom; and
(ii) C2 has a structural formula

wherein: X,Y,Z and M are as defined above:
(iii) "H2" is a halogen atom; and
(iv) W is as defined above; wherein the improvement comprises using an amount of M such that the first reacted mixture comprises an excess of M in an amount of less than 100%, and wherein the yield of C3 is greater than 70 percent, and wherein the second halide is added to the first reacted mixture in situ.

2. The process of claim 1 wherein M is selected from sodium, potassium and lithium.
3. The process of claim 2 wherein M is sodium.
4. The process of claim 2 wherein M is potassium.
5. The process of claim 2 wherein M is lithium.
6. The process of claim 1 wherein "H1" is chlorine or bromine.
7. The process of claim 6 wherein "H1" is chlorine.
8. The process of claim 1 wherein "H2" is chlorine or bromine.
9. The process of claim 8 wherein "H2" is chlorine.
10. The process of claim 1 wherein X is aryl or alkyl.
11. The process of claim 10 wherein Y is aryl or alkyl.
12. The process of claim 11 wherein X is aryl.
13. The process of claim 12 wherein Y is aryl.
14. The process of claim 13 wherein X and Y are both phenyl.
15. The process of claim 1 wherein W is aryl or alkyl.
16. The process of claim 15 wherein W is alkyl containing from 1 to 40 carbon atoms.
17. The process of claim 16 wherein W contains at least 6 carbon atoms.
18. The process of claim 16 wherein W contains up to 26 carbon atoms.
19. The process of claim 1 wherein S is selected from the group consisting of di-n-butyl ether, toluene, tetrahydrofuran, and p-dioxane.
20. The process of claim 19 wherein S is di-n-butyl ether.
21. The process of claim 1 wherein C3 is a liquid.
22. The process of claim 21 wherein the molar conversion efficiency, E1, from C1 to C3, is greater than 80 mole percent.
23. The process of claim 22 wherein E1 is greater than 90 mole percent.
24. The process of claim 21 wherein the molar conversion efficiency, E2, from C2 to C3, is greater than 80 mole percent.
25. The process of claim 24 wherein E2 is greater than 80 mole percent.
26. The process of claim 21 wherein C3 is n-hexyldiphenylphosphine.

27. The process of claim 26 wherein E1 is greater than 80 mole percent.

28. The process of claim 21 wherein C3 is a solid.

29. The process of claim 29 wherein C3 is n-eicosyldiphenylphosphine.

30. The process of claim 29 wherein the second reacted mixture comprises phosphine oxides in an amount of less than 2 percent by weight.

31. The process of claim 28 wherein C3 is behenyldiphenylphosphine.

32. The process of claim 31 wherein the second reacted mixture comprises phosphine oxides in an amount of less than 2 percent by weight.

33. The process of claim 21 wherein C3 is a gas.

34. The process of claim 1 wherein the second reacted mixture comprises less than 2% by weight of an oxide of C3 based on the weight of C3.

35. The process of claim 34 wherein the oxide of C3 is present in an amount of less than 1% by weight.

36. The process of claim 1 wherein the excess of M is at least 5% by weight.

37. The process of claim 1 wherein the excess of M is less than 50% by weight.

38. The process of claim 37 wherein the excess of M is less than 40% by weight.

39. The process of claim 38 wherein the excess of M is more than 5% by weight.

40. The process of claim 39 wherein the excess of M is more than 20 percent by weight.

41. The process of claim 1 wherein M is in the form of particles having diameters less than 5000 microns.

42. The process of claim 41 wherein M is in the form of particles having diameters less than 1000 microns.

43. The process of claim 42 wherein the particles are prepared by passing them through a homogenizer.

44. The process of claim 1 which comprises adding C1 gradually over a period of less than 20 hours until there is no excess of M.

45. The process of claim 16 wherein the second halide is 1,12-dihalododecane.

46. The process of claim 1 wherein W comprises a silicon radical.

47. The process of claim 46 wherein C3 is diphenyl(trimethylsilyl)phosphine or dimethyl(trimethylsilyl)phosphine.

48. The process of claim 1 wherein the first step comprises initiating the first reaction by adding up to about 5% of a molar amount of the first halide.

49. The process of claim 1 wherein the second step further comprises adding a hydroxylic solvent to remove excess sodium.

50. The process of claim 49 wherein the hydroxylic solvent is methanol or ethanol.

51. The process of claim 1 wherein Z is phosphorus and which comprises a first step wherein the reaction temperature is temporarily reduced to a temperature in the range from $T_m$°C. to $(T_m+20)$°C., wherein $T_m$ is the melting point of the metal M or amalgam.

52. Behenyldiphenylphosphine.

* * * * *

UNITED STATES PATENT AND TRADEMARK OFFICE
CERTIFICATE OF CORRECTION

PATENT NO.   : 4,618,720
DATED        : October 21, 1986
INVENTOR(S)  : W. Elliott Bay et al.

It is certified that error appears in the above–identified patent and that said Letters Patent are hereby corrected as shown below:

Col. 11, line 4, "claim 29" should be --claim 28--.

Signed and Sealed this

Tenth Day of March, 1987

*Attest:*

DONALD J. QUIGG

*Attesting Officer*

*Commissioner of Patents and Trademarks*